United States Patent [19]

Mix

[11] Patent Number: 4,582,570
[45] Date of Patent: Apr. 15, 1986

[54] AZEOTROPIC DEHYDRATION DISTILLATION PROCESS

[75] Inventor: Thomas W. Mix, Wellesley, Mass.

[73] Assignee: Merix Corporation, Wellesley, Mass.

[21] Appl. No.: 505,774

[22] Filed: Jun. 20, 1983

Related U.S. Application Data

[63] Continuation-in-part of Ser. No. 289,041, Jul. 24, 1981, abandoned.

[51] Int. Cl.$^4$ ............................................. B01D 3/36
[52] U.S. Cl. ........................................ 203/16; 203/18; 203/19; 203/63; 203/67; 562/608; 568/916
[58] Field of Search ...................... 203/14–19, 203/67, 57, 63, 64, 59; 568/913, 916; 562/608

[56] References Cited

U.S. PATENT DOCUMENTS

| | | | |
|---|---|---|---|
| 1,676,735 | 7/1928 | Keyes | 203/19 |
| 2,028,801 | 1/1936 | Othmer | 203/67 X |
| 3,433,788 | 3/1969 | Somekh et al. | 203/67 X |
| 4,217,178 | 8/1980 | Katzen et al. | 203/19 |
| 4,246,073 | 1/1981 | Umeda et al. | 203/25 |
| 4,358,536 | 11/1982 | Thorsson et al. | 203/19 X |

Primary Examiner—Wilbur Bascomb

[57] ABSTRACT

Improvement in an azeotropic distillation process, the improvement being the use of an entrainer characterized in that it is an organic compound in which one or more hydrogen atoms are replaced by halogen atoms, including at least one fluorine atom; it is miscible, under process conditions, with the organic compound being dehydrated; its volatility is sufficiently close to the volatility of the organic compound being dehydrated such that, under the process conditions, it forms an azeotrope with the organic compound; it is less miscible, under process conditions, with water than is the corresponding organic compound in which the halogen atoms are replaced with hydrogen atoms; and it is chemically stable under the process conditions.

15 Claims, 2 Drawing Figures

1

AZEOTROPIC DEHYDRATION DISTILLATION PROCESS

BACKGROUND OF THE INVENTION

This application is a continuation-in-part of Mix, "Entrainers", Ser. No. 289,041, filed July 24, 1981 and now abandoned.

This invention relates to entrainers used in azeotropic distillation processes and to extractants used in extraction processes.

Azeotropic distillation processes for removing water from a mixture containing water and an organic compound to be dehydrated, e.g. ethanol, which is difficult to dehydrate, commonly involve feeding the mixture to an azeotropic distillation column containing an entrainer having a greater affinity for the organic compound to be dehydrated than for water, whereby the mixture contacts the entrainer, reboiling the azeotropic distillation column to volatilize the water and the entrainer to remove the water and the entrainer from the organic compound, and recovering the dehydrated, entrainer-free organic compound.

Extraction processes for removing water from a mixture containing water and an organic compound to be dehydrated commonly involve contacting the mixture with an extractant having a greater affinity for the organic compound to be dehydrated than for water whereby a comparatively organic compound-rich extraction phase and a comparatively water-rich phase are formed, separating out the extraction phase, removing the extractant from the extraction phase, and recovering the dehydrated, extractant-free organic compound.

SUMMARY OF THE INVENTION

In general, in one aspect, the invention features an improvement in an azeotropic distillation process, the improvement being the use of an entrainer characterized in that it is an organic compound in which one or more hydrogen atoms are replaced by halogen atoms, including at least one fluorine atom; it is miscible, under process conditions, with the organic compound being dehydrated; its volatility is sufficiently close to the volatility of the organic compound being dehydrated such that, under the process conditions, it forms an azeotrope with the organic compound; it is less miscible, under process conditions, with water than is the corresponding organic compound in which the halogen atoms are replaced with hydrogen atoms; and it is chemically stable under the process conditions.

In preferred embodiments, there is associated with the azeotropic distillation column a concentrating column wherein water is removed from a mixture containing the organic compound and water to concentrate a portion of the organic compound, the resulting concentrated organic compound being vaporized and fed to the azeotropic distillation column, there being associated with the concentrating column condensing means to which a portion of the vapor is fed and in which that portion is condensed, the condensate returning to the concentrating column as reflux, the condensing means also serving as reboiling means for the azeotropic distillation column; the mixture is fed to the azeotropic distillation column in the form of vapor; the vapor comprises 80 mol percent or less of the organic compound to be dehydrated; the entrainer contains six or fewer carbon atoms; the entrainer contains at least one non-fluorine halogen atom, preferably chlorine, bromine, or both; at least 50% of the halogen atoms in the entrainer are fluorine atoms; the entrainer is a saturated hydrocarbon, preferably containing six or fewer carbon atoms, in which at least 50%, most preferably all, of the hydrogen atoms are replaced by halogen atoms; and the entrainer is 1,1,1-trichloropentafluoropropane, 1,1,2 trichloropentafluoropropane, trichlorotrifluoroethane, or a compound having a volatility as low as or lower than that of trichlorotrifluoro-ethane.

In other preferred embodiments the entrainer is an ether e.g. $CF_3OCFClCF_2Cl$ or $CF_3OOCF_2CFCl_2$; a halogenated olefin containing four or five carbon atoms and in which the carbon-carbon double bond is internal, i.e., it is not between either pair of carbon atoms at the ends of the molecule; a halogenated amine of the formula

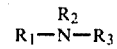

in which each $R_1$, $R_2$, and $R_3$, independently, is an alkyl group containing four or fewer carbon atoms, provided that the amine contains six or fewer carbon atoms and at least a fluorine atom; or an organic sulfur pentafluoride, of the formula $R\text{-}SF_5$, wherein R is an organic group (preferably an alkyl group) containing four or fewer carbon atoms and at least a fluorine atom.

In another aspect, the invention features the use, in an extraction process, of an extractant characterized in that it is an organic compound in which one or more hydrogen atoms are replaced by halogen atoms, it contains at least one fluorine atom, it is less miscible with water than is the corresponding organic compound in which said one or more halogen atoms are replaced with hydrogen atoms, and it is chemically stable under process conditions.

The halogenated entrainers and extractants of the invention provide the advantages of inertness and low toxicity. In addition, their high liquid density increases column throughput and facilitates phase separation. The selectivity, i.e., poor miscibility with water relative to miscibility with the organic compound being dehydrated, provided in part by the fluorine atoms of the new entrainers, saves energy in azeotropic distillation processes by reducing reflux requirements and permitting low (below 80 mol percent) organic compound content in the vapor sent to the final azeotropic distillation column. The efficiency of the entrainers also permits the energy-saving heat cascading of concentrating and azeotropic distillation columns.

Other advantages and features of the invention will be apparent from the following description of the preferred embodiments thereof, and from the claims.

DESCRIPTION OF THE PREFERRED EMBODIMENTS

We turn now to a description of the preferred embodiments of the invention, after first briefly describing the drawings.

ENTRAINERS

Figure 1:
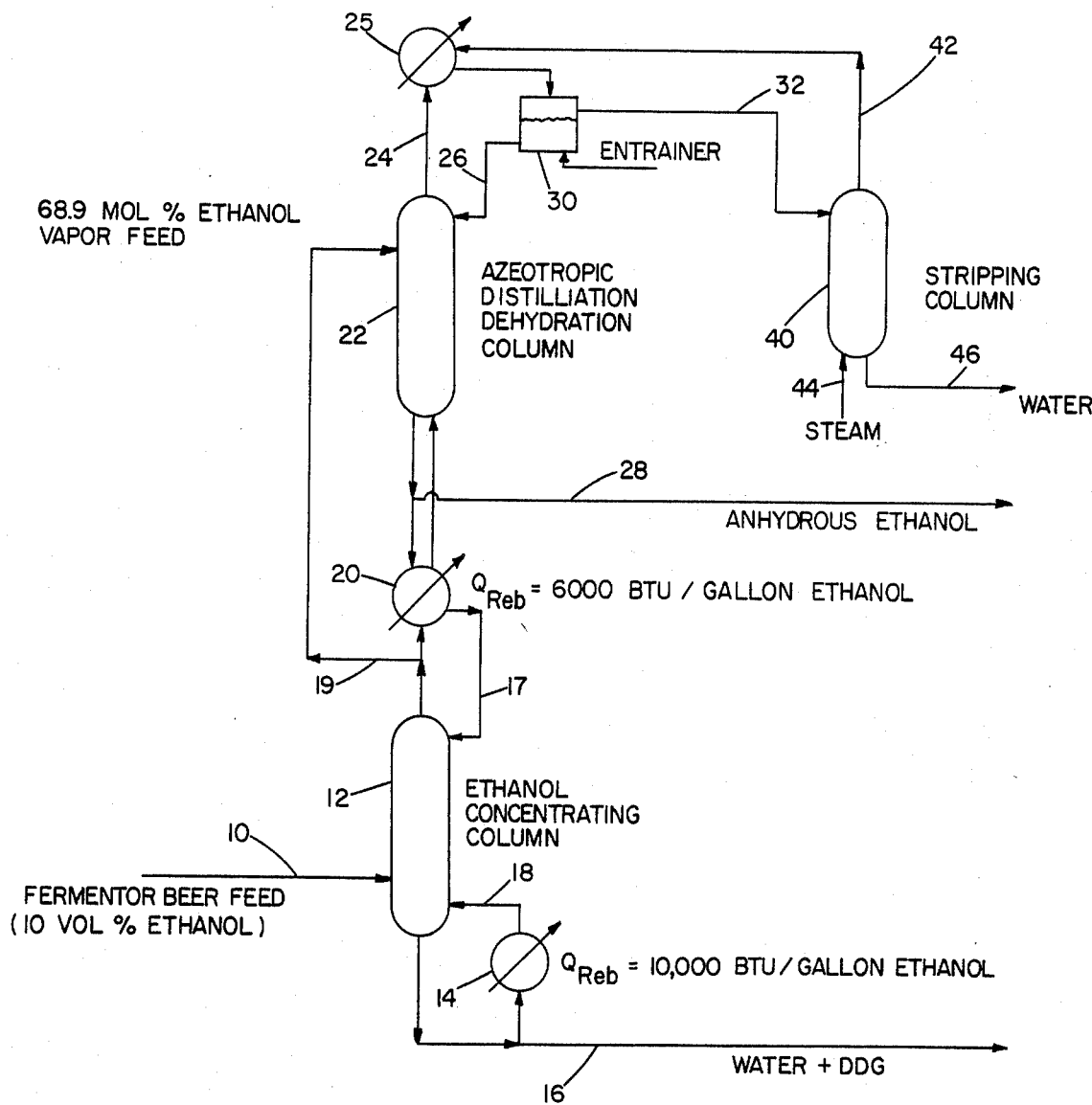
FIG. 1 and FIG. 2 are diagrammatic representations of azeotropic distillation apparatus embodying the invention.

The choice of the particular entrainer to be used under a given set of circumstances depends on process conditions and on the characteristics of the organic compounds being dehydrated. Four variable entrainer characteristics which should be taken into account in making this choice are (1) volatility; (2) miscibility with the organic compound being dehydrated; (3) miscibility with water; (4) chemical stability under process conditions. These characteristics can be generally related to entrainer composition, as follows.

First, as a general rule, an entrainer's volatility is inversely proportional to its molecular weight. Increasing the entrainer's molecular weight also, in general, lowers the entrainer's miscibility with water; an exception to this general rule is that halogenated pentane analogs are less miscible in water than are halogenated analogs of hexane and cyclohexane. For most purposes, the entrainer will contain six or fewer carbon atoms.

Volatility and miscibility are also influenced by the class of halogen-substituted organic compound being employed as the entrainer. Generally, the entrainer is a halogenated analog of a hydrocarbon (saturated or unsaturated), an ether, a tertrary amine, or an organic sulfur pentafluoride. Generally, the ether analogs are more miscible with water and with the organic compound to be dehydrated than are the hydrocarbon analogs having the same number of carbon atoms. Thus an ether entrainer will have a different halogen content than a hydrocarbon entrainer having the same number of carbon atoms which is used for the same purpose.

The degree to which an entrainer's hydrogen atoms are replaced by halogens, and the choice and distribution of halogen atoms are the other major factors influencing the characteristics of entrainers. Generally, fluorine atoms advantageously confer selectivity on an entrainer; i.e. fluorine atoms provide poor miscibility with water relative to miscibility with the organic compound being dehydrated. A high ratio of fluorine atoms to other halogen atoms (e.g. chlorine or bromine) also produces entrainers having lower boiling points (i.e. higher volatilities) than entrainers in which more fluorine atoms are replaced by other halogen atoms. For many applications it is preferred that the entrainer contain at least one or two non-fluorine halogen atoms in addition to fluorine atoms, to raise the boiling point to near that of the compound being dehydrated.

Using halogen atoms other than fluorine also can increase the miscibility of the entrainer with the organic compound and with water compared to an entrainer containing only fluorine atoms. In the case of ether analog entrainers, the non-fluorine halogen:fluorine ratio is generally lower than for hydrocarbon analog entrainers because ethers are generally more miscible with water and organic compounds than are hydrocarbons. The effect of non-fluorine halogen atoms on miscibility of ether analog entrainers is generally greatest when the halogen is bonded to a carbon atoms adjacent the ether linkage, and diminishes remote from that linkage.

The degree to which the hydrogen atoms of the entrainer are replaced by halogen atoms influences the characteristics of the entrainer. Generally, greater substitution of halogen for hydrogen decreases miscibility with water and decreases volatility; 50% or greater substitution is generally preferred.

The currently most preferred entrainers for use in the dehydration of ethanol, isopropyl alcohol, and acetic acid is 1,1,1 and 1,1,2-trichloropentafluoropropane (TCPFP), isomers of a saturated hydrocarbon in which all of the hydrogen atoms have been replaced with halogen atoms, over half of the halogen atoms being fluorine atoms. TCPFP isomers are made by halogenating pentane using conventional methods. 1,1,1-TCPFP has a boiling point of 74° C., in the right range for the formation of azeotropes with many fairly volatile organic compounds such as ethanol, isopropyl alcohol, and acetic acid, particularly at pressures near atmospheric. 1,1,1-TCPFP also exhibits a high activity coefficient with water, i.e. it has low water miscibility, permitting the use of minimal refluxing. 1,1,1-TCPFP also advantageously exhibits good miscibility with organic compounds such as ethanol, isopropyl alcohol, and acetic acid. In a system using stainless steel components, the 1,1,2-isomer is preferred because it is less reactive with stainless steel.

At elevated pressures, it can be advantageous to employ an entrainer which is more volatile than TCPFP, e.g. the commercially available refrigerant trichlorotrifluoroethane ("refrigerant 113", duPont).

Where higher water and organic compound miscibility are desired, it can be advantageous to use an organic entrainer which is not a hydrocarbon, e.g. an ether such as $CF_3OCFCLCF_2CL_2$ or $CF_3OCF_2CFCL_2$.

DETAILED DESCRIPTION OF THE DRAWING

There is shown in FIG. 1 ethanol distillation dehydration apparatus designed to be used with the method of the invention. Dilute feed (e.g. fermentor beer) enters ethanol concentrating column 12 via line 10. Steam generated in reboiler 14 enters column 12 via line 18 and strips the beer of its alcohol. Water and distillers' dark grains (DDG) leave column 12 via line 16. Reflux is supplied to the column via line 17 from condenser 20, enabling rectification of the ethanol from the water and permitting column 12 to produce an overhead vapor product containing 68.9 mole% ethanol. This vapor product enters azeotropic distillation dehydration column 22 via line 19. The overhead vapors from column 12 reboil column 22 via reboiler 20, such that columns 12 and 22 are arranged in an energy-efficient "cascade" configuration.

In column 22 the vapor contacts a suitable entrainer of the invention (e.g. trichloropentafluoropropane) fed to column 22 from liquid-liquid decanter 30 via line 26. The entrainer has a greater affinity for the ethanol of the ethanol/water vapor than for the water in the vapor, so the water becomes more volatile with respect to the entrained ethanol. The volatility relationship between entrainer and ethanol are such that the entrainer is stripped from the ethanol in the bottom trays of the column 22 and anhydrous ethanol is recovered as the bottom product of column 22 via line 28.

The overhead from column 22 is fed to a condenser via line 24 and the condensate is separated in decanter 30 into a heavy organic phase (the entrainer is denser than water) which is returned to column 22 as reflux via line 26, and a water phase which is fed via line 32 to stripping column 40. Steam is supplied to column 40 via line 44 to strip ethanol and entrainer from the water. Water leaves the column via line 46 and the overhead vapors containing the stripped ethanol and entrainer are fed to condenser 25 via line 42.

LIQUID FEED ETHANOL DEHYDRATION

Figure 2:
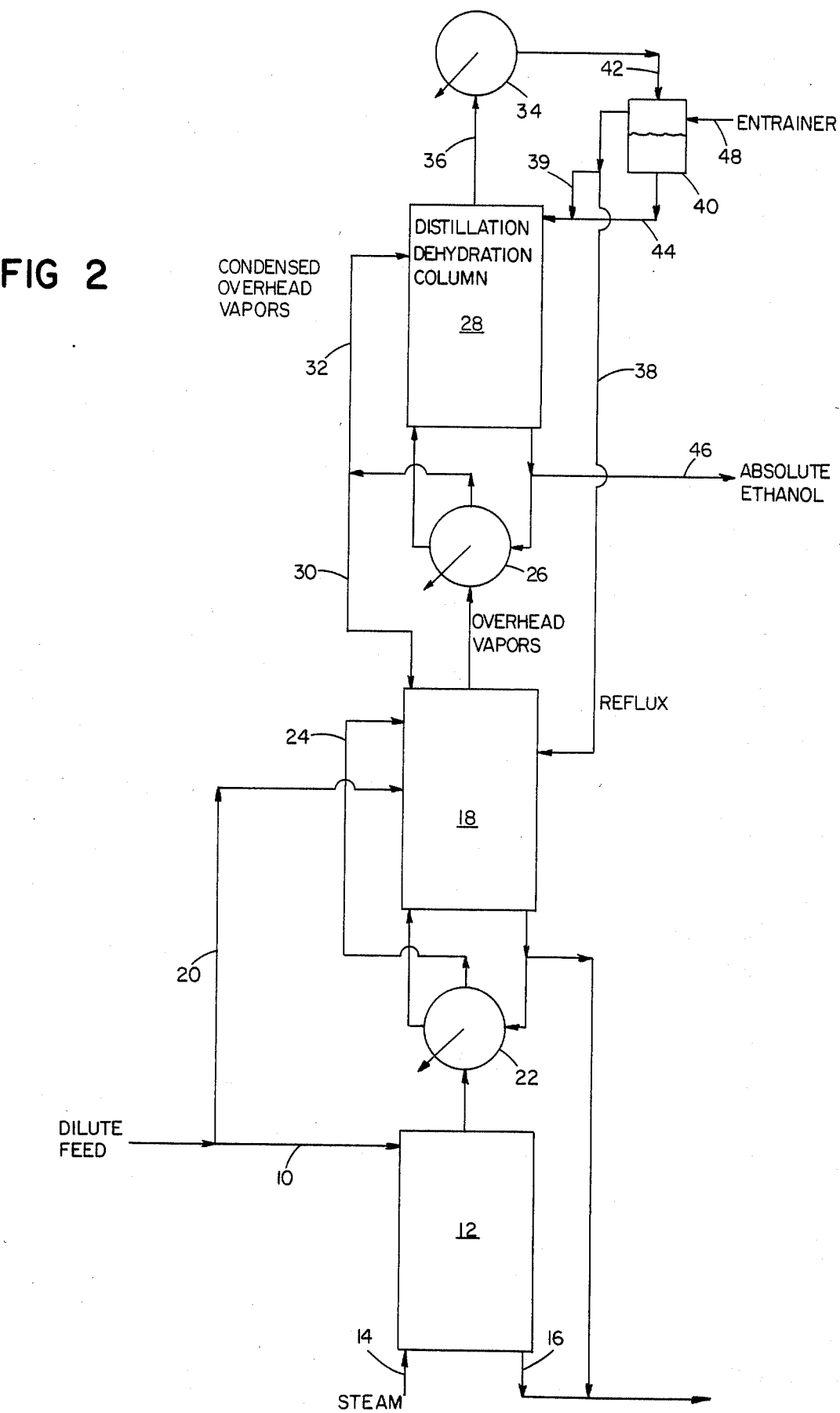

There is shown in FIG. 2 another preferred embodiment of ethanol distillation dehydration apparatus designed to be used with the method of the invention. Dilute feed (e.g., fermentor beer) enters high pressure column 12 via line 10. Steam, at a pressure of 120 psia, enters column 12 via line 14 and strips of beer of its alcohol. Water leaves column 12 via line 16. A portion of the dilute feed is fed to column 18 via line 20. The vapors from column 12, which contain 25 mol percent ethanol, reboil, by means of reboiler 22, the contents of column 18, and also enrich its alcohol content; the condensed vapors from column 1 enter column 18 via line 24.

The overhead vapors from column 18, at a temperature of 380° K., a pressure of 38 psia, and having an ethanol content of 75%, reboil, by means of reboiler 26, the contents of azeotropic distillation dehydration column 28. A portion of the condensed overhead vapor from column 18 returns to column 18 as reflux via line 30, while the remainder is fed to column 28 as liquid, via line 32, for absolute ethanol production. Column 28 contains recirculating entrainer (e.g. 1,1,1 trichloropentafluorpropane). The entrainer has a greater affinity for the ethanol of the ethanol/water mixture in column 28 than for water, so that the water becomes more volatile with respect to the entrained ethanol. The volatility relationships between the entrainer and the ethanol are such that the entrainer is stripped from the ethanol in the bottom trays of column 28, and absolute ethanol is thus recovered as the bottom product of column 28 via line 46.

The overhead vapors from column 28 enter, via line 36, condensor 34. The condensed liquid is then fed, via line 42, to phase separator 40, where it is separated into a predominantly aqueous and a predominantly alcohol-/entrainer phase. A portion of the aqueous phase is fed, via line 38, to column 18 as reflux, while the remainder is fed, via lines 39 and 44, to column 28. The alcohol/entrainer phase is fed to column 28 via line 44. Entrainer is replenished, as needed, to phase separator 40 via line 48. The efficiency of the entrainer enables the illustrated system to operate with a reduced reflux requirement (and thus a reduced energy requirement). The low (75%) alcohol content of the overhead product from column 18, adequate for dehydration with the chlorofluorinated entrainer, also represents a significant energy savings.

OTHER EMBODIMENTS

Other embodiments are within the following claims. For example, many different system designs can be used in conjunction with the organic entrainers of the invention; the choice depends on the compound being dehydrated and on the entrainer being used.

In a system such as that shown in FIG. 1, for example, rather than using the heat-cascading arrangement of columns shown therein, a water cooled condenser may be used to condense the overhead vapors from column 12 and a steam heated reboiler used to reboil column 22. The use of such separate heat exchangers increases the steam requirements of the process but permits column 12 to operate at lower pressure and reboiler 14 to use lower pressure steam than in the heat-cascaded case shown in FIG. 1.

In some cases it will be advantageous to use, in conjunction with the method of the invention, specialized distillation or extraction internals such as those described in U.S. Pat. No. 3,722,839, utilizing countercurrent flow within and countercurrent flow between stages and exhibiting very high stage efficiencies.

The method of the invention can be used to facilitate the dehydration of any organic compound, e.g., acetic acid, isopropyl alcohol, and cellosolves such as methyl cellosolve, which are difficult to dehydrate.

I claim:

1. In an azeotropic distillation process for removing water from a mixture containing water and an organic compound to be dehydrated comprising the steps of
    feeding said mixture to an azeotropic distillation column containing an entrainer having a greater affinity for said organic compound to be dehydrated than for water, whereby said mixture contacts said entrainer,
    reboiling said azeotropic distillation column to volatilize said water and said entrainer to remove said water and said entrainer from said organic compound, and
    recovering the dehydrated, entrainer-free organic compound, the improvement wherein
    said entrainer is an organic compound characterized in that
    it contains at least one fluorine atom, and at least one halogen atom other than a fluorine,
    it is miscible, under process conditions, with said organic compound being dehydrated,
    its volatility is sufficiently close to the volatility of said organic compound being dehydrated, such that, under said process conditions, it forms an azeotrope with said organic compound being dehydrated,
    it is less miscible with water than is the corresponding organic compound in which said one or more halogen atoms are replaced with hydrogen atoms, under process conditions, and
    it is chemically stable under said process conditions.
2. In the process of claim 1, the improvement wherein said other halogen is chlorine.
3. In the process of claim 1, the improvement wherein said other halogen is bromine.
4. In the process of claim 1, the improvement wherein said entrainer is a saturated halogen substituted hydrocarbon.
5. In the process of claim 1, the improvement wherein said entrainer is an ether.
6. In the process of claim 4, the improvement wherein all of the hydrogen atoms in said entrainer are replaced by halogen atoms.
7. In the process of claim 1 or 6, the improvement wherein said entrainer is trichlorotrifluoroethane.
8. In the process of claim 1 or 6, the improvement wherein said entrainer is 1,1,1-trichloropentafluoropropane.
9. In the process of claim 1 or 6, the improvement wherein said entrainer is 1,1,2-trichloropentafluoropropane.
10. In the process of claim 5, the improvement wherein said entrainer is $CF_3OCFClCF_2Cl$.
11. In the process of claim 5, the improvement wherein said entrainer is $CF_3OCF_2CFCl_2$.
12. In the process of claim 1, the improvement wherein said organic compound is ethanol.
13. In the process of claim 1, the improvement wherein said organic compound is isopropyl alcohol.
14. In the process of claim 1, the improvement wherein said organic compound is acetic acid.
15. In the process of claim 1, the improvement wherein said entrainer has a volatility as low as or lower than that of trichlorotrifluoroethane.

* * * * *